| United States Patent [19] | [11] | 4,127,661 |
| --- | --- | --- |
| Falconnet et al. | [45] | Nov. 28, 1978 |

[54] PIPERAZINE ALKANOLS

[75] Inventors: Bernard Falconnet, Bretigny-sur-Orge; Henri Pinhas, Paris, both of France

[73] Assignee: Serdex - Societe d'Etudes, de Recherches, de Diffusion et d'Exploitation, Puteaux, France

[21] Appl. No.: 782,051

[22] Filed: Mar. 28, 1977

[30] Foreign Application Priority Data

Apr. 7, 1976 [GB] United Kingdom ............... 14112/76

[51] Int. Cl.$^2$ ................. C07D 295/08; A61K 31/495
[52] U.S. Cl. .................................... 424/250; 544/401; 544/399

[58] Field of Search ..................... 260/268 R; 424/250

[56] References Cited

U.S. PATENT DOCUMENTS 3,959,359  5/1976  Pinhas .............................. 260/501.18

OTHER PUBLICATIONS

Ferlux, Chemical Abstracts, vol. 77, 48508p (1972).

*Primary Examiner*—Jose Tovar
*Attorney, Agent, or Firm*—Young & Thompson

[57] ABSTRACT

This invention relates to variously substituted piperazine derivatives. Said compounds possess therapeutically useful vasodilator properties.

5 Claims, No Drawings

PIPERAZINE ALKANOLS

This invention relates to new piperazine derivatives, to a process for their preparation and to their applications, particularly for therapeutic purposes.

This invention relates to compounds of the general formula:

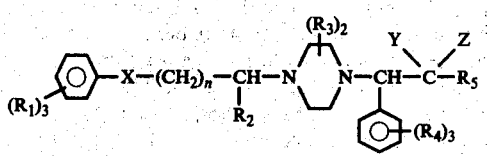

in which:
the substituents $R_1$ represent independently from each other a hydrogen atom, a halogen atom, a trifluoromethyl radical, a $C_{1-6}$ alkyl radical, a $C_{1-6}$ hydroxyalkyl radical, a $C_{1-6}$ alkoxy radical, a $C_{1-6}$ alkylcarbonyl radical or a $C_{3-7}$ cycloalkylcarbonyl radical or, together with the benzene nucleus to which they are attached, two of said substituents form another benzene nucleus,
$R_2$ represents a hydrogen atom or a $C_{1-6}$ alkyl radical,
the substituents $R_3$ represent independently from each other a hydrogen atom or a $C_{1-6}$ alkyl radical,
the substituents $R_4$ represent independently from each other a hydrogen atom, a halogen atom, a trifluoromethyl radical, a $C_{1-6}$ alkyl radical or a $C_{1-6}$ alkoxy radical,
$R_5$ represents a $C_{1-6}$ alkyl radical or a radical of the formula:

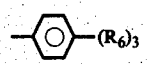

in which $R_6$ has the meaning given for $R_1$,
X represents an oxygen or sulfur atom,
n is an integer from 1 to 3,
Z is a hydrogen atom, and Y is a hydroxy radical, a $C_{1-6}$ alkoxy radical or a $C_{1-6}$ alkanoyloxy radical, or Y and Z, when taken together, represent an oxygen atom, and their pharmaceutically acceptable acid addition salts.

An advantageous class of the compounds of the formula (I) comprises compounds of the formula (Ia)

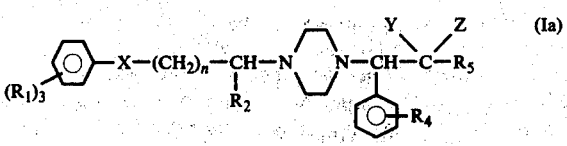

in which:
the substituents $R_1$ represent independently from each other a hydrogen atom, a halogen atom, a $C_{1-6}$ alkyl radical, a $C_{1-6}$ hydroxyalkyl radical, a $C_{1-6}$ alkoxy radical, a $C_{1-6}$ alkylcarbonyl radical or, together with the benzene nucleus to which they are attached, two of said substituents form another benzene nucleus,
$R_2$ represents a hydrogen atom or a $C_{1-6}$ alkyl radical,
$R_4$ represents a hydrogen atom, a trifluoromethyl radical, or a $C_{1-6}$ alkoxy radical,
$R_5$ represents a $C_{1-6}$ alkyl radical or a phenyl radical,
X represents an oxygen or sulfur atom,
n is an integer from 1 to 3 inclusive,
Z is hydrogen, and
Y is a hydroxy radical, a $C_{1-6}$ alkoxy radical or a $C_{1-6}$ alkanoyloxy radical, or
Y and Z, when taken together, represent an oxygen atom, and their pharmaceutically acceptable acid addition salts.

The acid addition salts may typically be those formed with hydrochloric, sulfuric, nitric, phosphoric, maleic, acetic, fumaric, lactic and citric acids.

Piperazine derivatives having a certain structural analogy have already been described in French Patent 75 10003. Said derivatives were predominantly described as having an analgesic activity.

To prepare compounds of the formula (I), an α-bromo ketone of the formula:

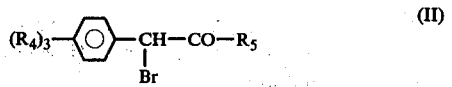

in which $R_4$ and $R_5$ have the above-defined meanings, may be reacted with a piperazine derivative of the formula:

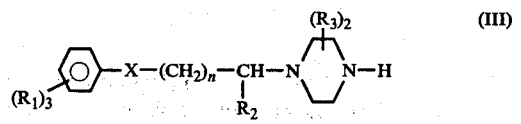

in which $R_1$, $R_2$, $R_3$ and n have the above-defined meanings, to give a compound of the formula (I) in which Y and Z represent together an oxygen atom and, if desired, the resulting ketonic compound may be reduced to the corresponding alcohol, i.e., to the corresponding compound of the formula (I) in which Z is a hydrogen atom and Y is a hydroxy radical and, if desired, the resulting alcohol may be converted to the corresponding alkyl ether or ester.

To prepare compounds of the formula (I) in which X is oxygen or sulfur, another embodiment comprises reacting the α-bromo ketone of the formula (II) with a piperazine derivative of the formula:

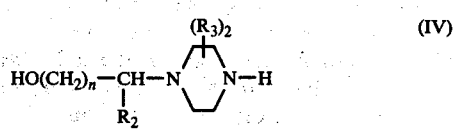

in which $R_2$, $R_3$ and n have the above-defined meanings, to give a compound of the formula:

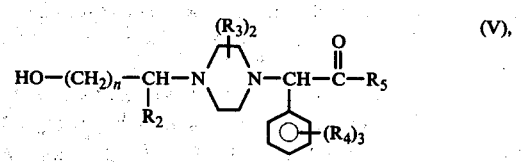

reacting the compound of the formula (V) with thionyl chloride, to give a compound of the formula:

$$\text{Cl}-(\text{CH}_2)_n-\underset{R_2}{\text{CH}}-\text{N}\underset{\diagdown\_\diagup}{\overset{(R_3)_2}{\diagup^\frown\diagdown}}\text{N}-\text{CH}-\underset{\underset{(R_4)_3}{\bigcirc}}{\overset{O}{\overset{\|}{C}}}-R_5 \quad \text{(VI)},$$

and then reacting the compound of the formula (VI), in the presence of a base, with a phenol or thiophenol of the formula:

$$(R_1)_3-\bigcirc-\text{XH} \quad \text{(VII)}$$

to give a compound of the formula (I) in which X is oxygen or sulfur and Y and Z represent together oxygen.

The resulting compound may then be converted to the other compounds of the formula (I) according to the above described method.

The compounds of the formula (II) used as starting materials may be obtained in conventional manner, by action of bromine on a compound of the formula:

$$(R_4)_3-\bigcirc-\text{CH}_2-\text{CO}-R_5 \quad \text{(VIII)}$$

The compounds of the formula (III) may be obtained in a conventional manner, by action of a derivative of the formula:

$$(R_1)_3-\bigcirc-X-(\text{CH}_2)_n-\underset{R_2}{\text{CH}}-A \quad \text{(IX)}$$

in which A is halogen or a methanesulfonate group, on a piperazine derivative of the formula:

$$\text{H}-\text{N}\underset{\diagdown\_\diagup}{\overset{(R_3)_2}{\diagup^\frown\diagdown}}\text{N}-\text{H} \quad \text{(X)}$$

The reaction of α-bromo ketone (II) with piperazine derivatives (III) or (IV) may be effected within a solvent such as benzene, an alcohol or a ketone. The reaction is preferably conducted at the refluxing temperature of the solvent, in the presence of an acid binding agent such as an alkali metal carbonate.

The reduction of the ketonic compounds to alcohols may be effected according to conventional methods, for example with $BH_4K$ in anhydrous methanol or by catalytic hydrogenation in the presence of platinum.

The reaction of compounds of the formula (V) with thionyl chloride may be effected according to the usual methods.

The reaction of compounds of the formula (VI) with phenols in the presence of a base may be effected typically within water and/or an alcohol, preferably at the refluxing temperature of the solvent.

The following non limiting Examples illustrate the preparation of compounds of the formula (I).

EXAMPLE 1

(a) Preparation of 1-bromo-1-phenyl acetone

Bromine (1 mole) is added dropwise to phenylacetone (1 mole) dissolved in dry benzene (800 cc), with stirring, over 1 hour, at room temperature. Within a few minutes, the initially coloured medium turns pale yellow. On completion of the addition, the organic phase is washed with ice-water to neutral pH, and is then dried over sodium sulfate, after which the benzene is removed in vacuo, over a water-bath, to give a green oil which may be distilled. B.p.: 125° C./0.2 mm Hg.

In practice, the benzene solution is used after drying to proceed with the synthesis.

(b) Preparation of 1-(N-β-hydroxyethyl-piperazino)-1-phenyl acetone

To a solution of 1-bromo-1-phenyl-acetone (1 mole) in dry benzene (800 cc) are added anhydrous potassium carbonate (1 mole) and N-β-hydroxyethyl-piperazine (1 mole). The resulting mixture is refluxed, with stirring, during 20 hours. After cooling, the benzene phase is washed with water to neutral pH and is then concentrated in vacuo, to give a brown oil which is then taken up into methylene chloride which is extracted with water made acidic with HCl. The aqueous phase is concentrated in vacuo over a waterbath; the resulting precipitate is taken up into boiling ethanol to which water is added to complete dissolution. On cooling, there are obtained white crystals (dihydrochloride) which, after suction filtering and drying in vacuo, melt at 240° C.

(c) Preparation of 1-(N-β-chloroethyl-piperazino)-1-phenylacetone

To 1-(N-β-hydroxyethyl-piperazino)-1-phenylacetone (1 mole) dissolved in methylene chloride (2 liters) is added thionyl chloride (2 moles) dropwise, at 0° C., with stirring. On completion of the addition, the resulting material is left aside 24 hours, at room temperature. The reaction medium is then poured over ice and sodium hydroxide (3 moles) is added thereto. The organic phase is washed with water to neutral pH. It is then dried over sodium sulfate and the solvent is evaporated off, to give a viscous brown oil which is used crude to proceed with the synthesis.

(d) Preparation of 1-[N-(2-phenoxy-1-ethyl)piperazino]-1-phenylacetone

Phenol (1 mole) and sodium hydroxide (1 mole) are dissolved in water (1.5 liter), after which 1-(N-β-chloroethyl-piperazino)-phenylacetone (1 mole) dissolved in ethanol (300 cc) is added thereto and the resulting material is refluxed with vigorous stirring during 24 hours. After cooling, the reaction medium is extracted with methylene chloride which is washed twice with N/10 aqueous sodium hydroxide and then with water to neutral pH. The solvent is evaporated off, to give a viscous oil which is taken up into a dilute aqueous hydrochloric acid solution and with diethyl ether. The aqueous phase is washed twice with diethyl ether and the aqueous phase is concentrated. The resulting precipitate is taken up into boiling ethanol to which water is added until dissolution is complete. On cooling, there are obtained white crystals (dihydrochloride) which, after suction filtering and drying in vacuo, melt at 137°–140° C.

N.M.R.: consistent.

EXAMPLE 2

Preparation of 1-[N-(2-phenoxy-1-ethyl)piperazino]-1-phenyl-2-propanol

To 1-(N-2-phenoxy-ethyl-piperazino)-1-phenylacetone (1 mole) dissolved in anhydrous methanol (1 liter) is added $BH_4K$ (1 mole) portionwise, at 0° C., with stirring. On completion of the addition (1 hour), the reaction mixture is stirred 24 hours at room temperature. The methanol is removed in vacuo over a waterbath, the resulting material is then taken up into methylene chloride which is washed with water to neutral pH. Concentration gives white crystals which melt at 100° C.

N.M.R.: consistent.

The product is dissolved in absolute ethanol to which is added a hydrochloric acid solution in ether, to acidic pH, to give white crystals (dihydrochloride) which melt at 197°–200° C.

N.M.R.: consistent.

EXAMPLE 3

(a) 2-(2-Methyl-1-phenoxy)-1-bromoethane

O-cresol (1 mole), sodium hydroxide (1 mole) and 1,2-dibromoethane (4 moles) are added to water (500 ml). The mixture is refluxed during 24 hours, with vigorous stirring. After cooling, the organic phase is decanted off and is then washed with a 5% sodium hydroxide solution, and then with water to neutral pH, after which it is dried over sodium sulfate and distilled, b.p. = 120° C./15 mm Hg.

(b) N[2-(2-methyl-1-phenoxy)-1-ethyl]piperazine 2-(2-Methyl-1-phenoxy)1-bromoethane (1 mole), sodium iodide (1 mole) and anhydrous piperazine (4 moles) are mixed with methyl ethyl ketone (1000 ml). The mixture is refluxed during 20 hours, with stirring. The solvent is removed in vacuo. The residue is taken up into water and sodium hydroxide (1 mole) is added thereto. The aqueous phase is extracted with ether. The organic phase is washed with water. The solvent is removed and the resulting oil is distilled. B.p. = 180° C./15 mm Hg.

(c) 1-(N[2-(2-methyl-1-phenoxy)-1-ethyl]piperazino)-1-phenyl-2-butanone

To N[2-(2-methyl-1-phenoxy)1-ethyl]piperazine (1 mole) dissolved in methyl ethyl ketone (1000 ml) are added anhydrous sodium carbonate (2 moles) of 1-bromo-1-phenyl-2-butanone (1 mole). The resulting mixture is refluxed during 5 hours, with stirring. The solvent is evaporated in vacuo over a water-bath and the residue is taken up into water. The aqueous phase is extracted with methylene chloride. The organic phase is washed with water to neutral pH, and a dilute aqueous hydrochloric acid solution is added thereto, with stirring. Decantation provides an intermediate methylene chloride-dilute aqueous hydrochloric acid solution oil phase. After separation, this oil phase is taken up into warm acetone. On cooling, there are obtained crystals which, after recrystallization from 95% ethyl alcohol, give white crystals which melt at 187°–190° C. N.M.R.: consistent.

EXAMPLE 4 —

1-(N-[2-(2-methyl-1-phenoxy)-1-ethyl]piperazino)-1-phenyl-2-butanol dihydrochloride To 1-(N[2-(2-methyl-1-phenoxy)-1-ethyl]piperazino)-1-phenylbutanone-2 (1 mole) dissolved in methanol (1000 ml) is added $BH_4K$ (1 mole) portionwise at 0° C., with stirring. Stirring is continued during 24 hours at room temperature. The methanol is removed in vacuo over a water-bath and the residue is taken up into water and diethyl ether. The organic phase is washed with water to neutral pH, dried over sodium sulfate and the solvent is evaporated off. The resulting white precipitate is taken up into ethanol to which is added an ethereal hydrochloric acid solution, to give white crystals which, after drying, melt at 247°–250° C.

EXAMPLE 5

(a) 1-Phenoxy-2-propanol

To phenoxy acetone (1 mole) dissolved in methanol (500 ml), is added $BH_4K$ (1 mole) portionwise at 0° C. Stirring is continued at room temperature during 24 hours. The methanol is removed in vacuo over a water-bath, the residue is taken up into water and ether. The organic phase is washed with water to neutral pH, after which the material is dried and the residual oil is distilled after removal of the solvent. B.p. = 139° C./20 mm Hg.

(b) 1-Phenoxy-2-propyl methane sulfonate

To 1-phenoxy-2-propanol (1 mole) dissolved in pyridine (500 ml) is added methane sulfochloride (1 mole) at a rate sufficient for the temperature of the reaction mixture to reach a value of 40°–50° C., with stirring. On completion of the addition, the reactor is sealed and the reaction mixture is left aside at room temperature during 48 hours. The reaction mixture is then poured over ice. The aqueous phase is extracted with methylene chloride. The organic phase is washed with dilute sulfuric acid and then with water to neutral pH. The resulting material is dried over sodium sulfate and concentrated, to give an oil which crystallizes. The material is taken up into ether, with stirring, to give a white precipitate which is suction filtered. M.p. = 58° C.

(c) N(1-Phenoxy-2-propyl)-piperazine

1-Phenoxy-2-propyl methane sulfonate (1 mole), anhydrous piperazine (4 moles) and potassium carbonate (2 moles) are added to 1000 ml methyl ethyl ketone. The mixture is refluxed during 45 hours, with stirring. The solvent is removed in vacuo and the residue is taken up into water and ether. The ethereal phase is again treated with a dilute aqueous hydrochloric acid solution and the aqueous phase is evaporated off. The resulting oil is taken up into a minimum amount of water. Sodium hydroxide (30 g) is added thereto, after which the material is extracted twice with ether. The ether is removed and the residual oil is distilled. B.p. = 104°–105° C./0.1 mm Hg. N.M.R.: consistent.

(d) 1-[N(1-phenoxy-2-propyl)piperazino]-1-phenyl acetone

To N(1-phenoxy-2-propyl)piperazine (1 mole) dissolved in methylethylketone (1000 ml) are added dry potassium carbonate (2 moles) and 1-bromo-1-phenylacetone (1 mole). The mixture is refluxed during 5 hours, with stirring. The solvent is evaporated off in vacuo. The residue is taken up into water and is then extracted with methylene chloride. The organic phase is washed with water to neutral pH. The organic phase is extracted with a dilute aqueous hydrochloric acid solution and is then concentrated in vacuo, over a water-bath. The resulting oil is taken up into boiling 95% ethyl alcohol, to give, on cooling, white crystals, M.p. 177°–180° C. N.M.R.: consistent.

EXAMPLE 6

1-[N(1-phenoxy-2-propyl)piperazino]-1-phenyl-2-propanol

To 1-[N(1-phenoxy-2-propyl)piperazino]-1-phenylacetone (1 mole) dissolved in methanol (1000 ml) is added $BH_4K$ (1 mole), portionwise at 0° C. Stirring is continued during 24 hours at room temperature. The methanol is removed in vacuo and the residue is taken up into ether and water. The ether phase is washed with water to neutral pH. The ether is evaporated off. The resulting white precipitate is taken up into ethanol to which is added an ethereal solution of hydrochloric acid. The white crystals obtained after recrystallization from ethanol melt at 237°–240° C.

EXAMPLE 7

(a) 3-Phenoxy-1-chloro-propane

A mixture of phenol (1 mole), sodium hydroxide (1 mole) and 3-bromo-1-chloro-propane (2 moles) in water (1000 ml) and ethyl alcohol (250 ml) is refluxed during 20 hours, with stirring. After cooling, sodium hydroxide (30 g) is added to the reaction medium which is then extracted with methylene chloride. The organic phase is washed with water to neutral pH. It is then dried over sodium sulfate, concentrated in vacuo over a water-bath and the residual oil is distilled. B.p. = 118°–120° C./15 mm Hg.

(b) N-(3-phenoxy-1-propyl)piperazine

A mixture of 3-phenoxy-1-chloro-propane (1 mole), sodium iodide (1 mole) and anhydrous piperazine (4 moles) is added to methyl ethyl ketone (1000 ml). The mixture is refluxed during 24 hours, with stirring. The solvent is removed in vacuo over a water-bath and the residue is poured over water. The aqueous phase is extracted with methylene chloride and then washed twice with water. The solvent is removed and the residual oil is distilled. B.p. = 115° C./0.05 mm Hg.

(c) 1-[N(3-phenoxy-1-propyl)-piperazino]-1-phenylacetone dihydrochloride

To methylethylketone (1000 ml) is added N(3-phenoxy-1-propyl)-piperazine (1 mole), dry potassium carbonate (2 moles) and 1-bromo-1-phenyl-acetone (1 mole). The resulting mixture is refluxed during 5 hours, with stirring. The solvent is removed and the residue is taken up into water and is then extracted with methylene chloride. The organic phase is washed with water to neutral pH and is then extracted with a dilute aqueous hydrochloric acid solution. The aqueous phase is washed with methylene chloride and is concentrated in vacuo. The resulting solid material is then recrystallized from 95% ethanol, suction filtered and dried, to give crystals, M.p. = 177°–180° C. N.M.R.: consistent.

EXAMPLE 8

1-[N(3-phenoxy-1-propyl)piperazino]-1-phenyl-2-propanol dihydrochloride $BH_4K$ (1 mole) is added portionwise, at 0° C. to 1-[N-(3-phenoxy-1-propyl)piperazino]-1-phenylacetone (1 mole) dissolved in methanol (500 ml). The reaction mixture is then stirred during 24 hours at room temperature. The solvent is removed in vacuo, the residue is taken up into water and ether. The organic phase is washed with water to neutral pH and the solvent is evaporated off. The resulting solid material is dissolved in ethanol to which is added an ethereal hydrochloric acid solution. The resulting precipitate is recrystallized from ethanol. M.p. = 177°–180° C. N.M.R.: consistent.

EXAMPLE 9

(a) 3-Phenylthio-1-chloro-propane

A mixture of thiophenol (1 mole), sodium hydroxide (1 mole) and 3-bromo-1-chloro-propane (2 moles) in water (1000 ml) and ethanol (250 ml) is refluxed during 20 hours, with stirring. After cooling, sodium hydroxide (30 g) is added to the reaction medium which is then extracted with methylene chloride. The organic phase is washed with water to neutral pH, after which it is dried over sodium sulfate, concentrated and distilled. B.p. = 165° C./15 mm Hg. N.M.R.: consistent.

(b) N(3-phenylthio-1-propyl)piperazine

To 1000 ml methyl ethyl ketone are added 3-phenylthio-1-chloro-propane (1 mole), sodium iodide (1 mole) and anhydrous piperazine (4 moles). The resulting mixture is refluxed during 24 hours, with stirring, after which the solvent is evaporated in vacuo, the residue is taken up into water and ether. The ether phase is washed with water, dried and concentrated. The residue is distilled in vacuo. B.p. = 140° C./0.05 mm Hg. N.M.R.: consistent.

(c) 1-[N(3-phenylthio-1-propyl)piperazino]-1-phenyl-2-pentanone dihydrochloride

To 1000 ml methyl ethyl ketone are added N(3-phenylthio-1-propyl)piperazine (1 mole), dry potassium carbonate (2 moles), and 1-bromo-1-phenyl-2-pentanone. The resulting mixture is refluxed during 5 hours, with stirring. The solvent is removed after which the residue is taken up into water and extracted with methylene chloride. The resulting material is washed with water and is then extracted with a dilute aqueous hydrochloric acid solution and concentrated in vacuo. The residual oil is recrystallized from an aqueous-alcoholic mixture, to give white crystals. M.p. 207°–210° C.

EXAMPLE 10

1-[N(3-phenylthio-1-propyl)piperazino]-1-phenyl-2-pentanol dihydrochloride

The compound is obtained from the compound of Example 9, by reduction with $BH_4K$, under the same conditions as described in Example 8. M.P. = 252°–255° C.

EXAMPLE 11

1-[N(2-phenoxy-1-ethyl)piperazino]-1-phenyl-2-propyl acetate dihydrochloride

1-[N(2-phenoxy-1-ethyl)piperazino]-1-phenyl-2-propanol (1 mole) dissolved in acetic anhydride (500 ml) is heated to 80° C. during 1 hour. The solution is then evaporated in vacuo over a water-bath and the residue is taken up into ether to which is added an ethereal solution of hydrochloric acid. The resulting precipitate is recrystallized from acetone. M.p. = 157°–160° C. N.M.R.: consistent.

The characteristics of dihydrochlorides of compounds of the formula (I) from Examples 1–11 are tabulated in the following Table, together with those of other dihydrochlorides prepared in an analogous manner.

TABLE I

| Ex. | $R_1$ | $R_2$ | $R_3$ | $R_4$ | $R_5$ | X | Y | Z | n | M.p.° C |
|---|---|---|---|---|---|---|---|---|---|---|
| 1 | H | H | H | H | $CH_3$ | O | | O | 1 | 137–140 |
| 2 | H | H | H | H | $CH_3$ | O | OH | H | 1 | 197–200 |
| 3 | 2-$CH_3$ | H | H | H | $C_2H_5$ | O | | O | 1 | 187–190 |
| 4 | 2-$CH_3$ | H | H | H | $C_2H_5$ | O | OH | H | 1 | 247–250 |
| 5 | H | $CH_3$ | H | H | $CH_3$ | O | | O | 1 | 177–180 |
| 6 | H | $CH_3$ | H | H | $CH_3$ | O | OH | H | 1 | 237–240 |
| 7 | H | H | H | H | $CH_3$ | O | | O | 2 | 177–180 |
| 8 | H | H | H | H | $CH_3$ | O | OH | H | 2 | 177–180 |
| 9 | H | H | H | H | $C_3H_7$ | S | | O | 2 | 207–210 |
| 10 | H | H | H | H | $C_3H_7$ | S | OH | H | 2 | 252–255 |
| 11 | H | H | H | H | $CH_3$ | O | $CH_3COO$ | H | 1 | 157–160 |
| 12 | 4-$CH_3O$ | H | H | H | $CH_3$ | O | | O | 1 | 192–195 |
| 13 | H | H | H | H | $C_6H_5$ | O | | O | 1 | 197–200 |
| 14 | H | H | H | H | $C_6H_5$ | O | OH | H | 1 | 182–185 |
| 15 | H | H | H | 3-$CF_3$ | $CH_3$ | O | | O | 1 | 137–140 |
| 16 | H | H | H | 3-$CF_3$ | $CH_3$ | O | OH | H | 1 | 152–155 |
| 17 | 3-$CH_3O$ | H | H | H | $CH_3$ | O | | O | 1 | 187–190 |
| 18 | 2-Cl | H | H | H | $CH_3$ | O | | O | 1 | 227–230 |
| 19 | 4-Cl | H | H | H | $CH_3$ | O | | O | 1 | 227–230 |
| 20 | 4-$CH_3CO$ | H | H | H | $CH_3$ | O | | O | 1 | 232–235 |
| 21 | 3-$CH_3CO$ | H | H | H | $CH_3$ | O | | O | 1 | 207–210 |
| 22 | 4-Cl | H | H | H | $CH_3$ | O | OH | H | 1 | 237–240 |
| 23 | 3,4-Benzo | H | H | H | $CH_3$ | O | | O | 1 | 227–230 |
| 24 | 4-$CH_3$ | H | H | H | $CH_3$ | O | | O | 1 | 217–220 |
| 25 | 2-$CH_3$ | H | H | H | $CH_3$ | O | | O | 1 | 187–190 |
| 26 | 2-$CH_3$ | H | H | H | $CH_3$ | O | OH | H | 1 | 267–270 |
| 27 | 3-$CH_3O$ | H | H | H | $CH_3$ | O | OH | H | 1 | 237–240 |
| 28 | 3,4-Benzo | H | H | H | $CH_3$ | O | OH | H | 1 | 227–230 |
| 29 | 2-Cl | H | H | H | $C_6H_5$ | O | | O | 1 | 247–250 |
| 30 | 4-$CH_3$ | H | H | H | $CH_3$ | O | OH | H | 1 | 227–230 |
| 31 | 3-$C_2H_4OH$ | H | H | H | $CH_3$ | O | OH | H | 1 | 197–200 |
| 32 | 2-Cl | H | H | H | $C_6H_5$ | O | OH | H | 1 | 262–265 |
| 33 | H | H | H | $CH_3O$ | $CH_3$ | O | | O | 1 | 247–250 |
| 34 | 2-$CH_3$ | H | H | H | $C_6H_5$ | O | | O | 1 | 217–220 |
| 35 | 3,4,5-$(CH_3O)_3$ | H | H | H | $C_6H_5$ | O | | O | 1 | 232–235 |
| 36 | 2,6-$(CH_3)_2$ | H | H | H | $C_6H_5$ | O | | O | 1 | 237–240 |
| 37 | 2,6-$(CH_3)_2$ | H | H | H | $CH_3$ | O | | O | 1 | 217–220 |
| 38 | H | H | H | H | $CH_3$—$CH_2$ | O | | O | 1 | 177–180 |
| 39 | 3,4,5-$(CH_3O)_3$ | H | H | H | $C_6H_5$ | O | OH | H | 1 | 247–250 |
| 40 | H | H | H | 4-$CH_3O$ | $CH_3$ | O | OH | H | 1 | 247–250 |
| 41 | 2-$CH_3$ | H | H | H | $C_6H_5$ | O | OH | H | 1 | 242–245 |
| 42 | 2,6-$(CH_3)_2$ | H | H | H | $C_6H_5$ | O | OH | H | 1 | 257–260 |
| 43 | 2,6-$(CH_3)_2$ | H | H | H | $C_2H_5$ | O | OH | H | 1 | 267–270 |
| 44 | H | H | H | H | $CH_3$ | S | | O | 1 | 157–160 |
| 45 | 2,6-$(CH_3)_2$ | H | H | H | $C_2H_5$ | O | | O | 1 | 227–230 |
| 46 | 2,6-$(CH_3)_2$ | H | H | H | $CH_3$ | O | OH | H | 1 | 252–255 |
| 47 | H | H | H | H | $C_2H_5$ | O | OH | H | 1 | 267–270 |
| 48 | 3,4,5-$(CH_3O)_3$ | H | H | H | $CH_3$ | O | | O | 1 | 177–180 |
| 49 | H | H | H | H | $CH_3$ | S | OH | H | 1 | 227–230 |
| 50 | H | H | H | H | $C_6H_5$ | O | | O | 2 | 237–240 |
| 51 | H | H | H | H | $C_6H_5$ | O | OH | H | 2 | 257–260 |
| 52 | 4-Cl | H | H | H | $CH_3$ | S | | O | 1 | 227–230 |
| 53 | H | H | H | H | $C_6H_5$ | S | | O | 1 | 247–250 |
| 54 | 4-Cl | H | H | H | $C_2H_5$ | S | | O | 1 | 207–210 |
| 55 | H | H | H | H | $CH_3$ | S | | O | 1 | 177–180 |
| 56 | 4-Cl | H | H | H | $C_6H_5$ | S | | O | 1 | 227–230 |
| 57 | H | H | H | H | $C_2H_5$ | S | | O | 1 | 197–200 |
| 58 | 4-Cl | H | H | H | $C_2H_5$ | S | OH | H | 1 | 247–250 |
| 59 | H | H | H | H | $CH_3$ | S | OH | H | 1 | 242–245 |
| 60 | H | H | H | H | $C_6H_5$ | S | OH | H | 1 | 242–245 |
| 61 | 4-Cl | H | H | H | $C_6H_5$ | S | OH | H | 1 | 257–260 |
| 62 | 4-Cl | H | H | H | $CH_3$ | S | OH | H | 1 | 247–250 |
| 63 | H | H | H | H | $C_2H_5$ | S | OH | H | 1 | 227–230 |
| 64 | H | H | H | H | $C_3H_7$ | O | | O | 1 | 167–170 |
| 65 | H | H | H | H | $C_3H_7$ | O | OH | | H | 1 | 197–200 |
| 66 | 2-$CH_3$ | H | H | H | $C_3H_7$ | O | | O | 2 | 207–210 |
| 67 | 2-$CH_3$ | H | H | H | $C_2H_5$ | O | | O | 2 | 222–225 |
| 68 | 2-$CH_3$ | H | H | H | $C_2H_5$ | O | OH | H | 2 | 237–240 |
| 69 | 2-$CH_3$ | H | H | H | $C_3H_7$ | O | OH | H | 2 | 247–250 |
| 70 | H | H | H | H | $C_3H_7$ | O | | O | 2 | 217–220 |

The compounds of the formula (I) and their pharmaceutically acceptable acid addition salts have vasodilator properties, and are useful therapeutically, particularly for the control of the cardio-vascular system, especially as peripheral vasodilators.

The results of pharmacological and toxicological investigations which demonstrate said properties are given below.

I. VASODILATOR ACTION 1.1 Procedure

The tests were conducted with pentobarbital anesthetized dogs (35 mg/kg/i.v.) under artificial respiration with pentobarbital infusion (5 mg/kg/hr).

The carotid arterial pressure was recorded by means of an electromagnetic capsule connected to the carotid artery. From said determination were calculated the mean blood pressure, the systolic pressure, the diastolic pressure and the pulse pressure.

The femoral rate of flow was recorded by means of an electromagnetic sensor placed around the femoral artery. Local peripheral resistance was calculated from said parameters.

1.2 Results

The compounds of the formula (I) were administered intravenously at a dosage of 5 mg/kg. Two tests were conducted with each compound.

All the compounds tested exhibited a peripheral vasodilator activity, said action being more or less intense and more or less durable.

Among said compounds, the compounds of Examples 1, 2 and 4 were found particularly valuable. More detailed results obtained with said products are given hereinafter.

II. ACTION OF THE COMPOUNDS OF EXAMPLES 1, 2 AND 4

2.1 Peripheral action

All three compounds exhibited a similar vasodilator activity, relatively intense and durable at a dosage of 2.5 mg/kg.

| Compounds | Femoral rate of flow | Local peripheral resistance |
|---|---|---|
| Example 4 | >30% 1 hour | 30% at 30mn |
| Example 1 | >25% 1 hour | 20% at 30mn |
| Example 2 | >100% injec. >15% 30mn | 15% at 30mn |

A transient decrease of the blood pressure is noted on injection, local peripheral resistance decreases with a concomitant increase of the femoral rate of flow during at least 30 minutes.

2.2 Study on the autonomic nervous system

The action of the compounds (2.5 mg/kg/i.v.) with respect to tensional effects of the occlusion of the carotids, of the stimulation of the central or peripheral end of the vagus, of acetylcholine, of noradrenaline, adrenaline and isoprenaline was studied in pentobarbital anesthetized (35 mg/kg/i.v.) dogs, both divagotomized and unvagotomized.

All three compounds exhibit a substantial adrenolytic activity which inhibits by a factor in excess of 50% the hypertensive effects of noradrenaline and adrenaline.

2.3 Study of the spasmolytic activity

The action of the compounds was studied on isolated organs, with respect to cholinergic and $BaCl_2$ induced contractions of the duodenum of rats and to the histaminic contractions of the ileum of guinea-pigs. All three compounds exhibit a non-specific musculotropic and neurotropic spasmolytic action at dosages within the range of from $10^{-7}$ to $10^{-6}$ M.

2.4 Acute toxicity

Acute toxicity was studied orally in male Sprague Dawley rats kept fasting 24 hours prior to the test, distributed in homogeneous groups of 10 animals each. The animals were given a single administration of the test materials and were kept under observation during 14 days.

The $LD_{50}$ were determined after 14 days at a probability threshold of $p = 0.05$, according to the method of Litchfield and Wilcoxon.

| Compounds | $LD_{50}$ mg/kg |
|---|---|
| Example 4 | 700 (600 – 800) |
| Example 1 | 800 (500 – 1200) |
| Example 2 | 250 (150– 400) |

Thus, this invention relates also to therapeutic compositions containing as active ingredient a compound of the formula (I) or a pharmaceutically acceptable acid addition salt thereof, typically together with a pharmaceutically acceptable excipient.

The therapeutic compositions of this invention may be administered to humans, typically by the oral or parenteral routes.

Said compositions may typically be formulated as capsules, tablets, or as injectable solutions.

Said composition may typically contain 1-60wt% of active ingredient according to the administration route.

For adults, the daily dosage regimen may be from 50 mg to 2000 mg active ingredient.

Having now described our invention what We claim as new and desire to secure by Letters Patent is:

1. A compound selected from the group consisting of compounds of the formula:

$$\text{(Ia)}$$

in which:
$R_1$ is selected from hydrogen, chlorine, methyl, hydroxyethyl, dimethyl, methoxy, trimethoxy and 3,4 benzo,
$R_2$ is selected from hydrogen and methyl,
$R_4$ is selected from hydrogen, trifluoromethyl and methoxy,
$R_5$ is selected from $C_{1-3}$ alkyl and phenyl,
X is selected from oxygen and sulfur,
n is an integer from 1 to 3 inclusive, and a pharmaceutically acceptable acid addition salt thereof.

2. 1-[N-2-(phenoxy-1-ethyl)piperazino]-1-phenyl-2-propanol and its pharmaceutically acceptable acid addition salts.

3. 1-(N-[2-(2-methyl-1-phenoxy)-1-ethyl]piperazino)-1-phenyl-2-butanol and its pharmaceutically acceptable acid addition salts.

4. A therapeutic composition having a vasodilator action containing a vasodilator effective amount of a compound selected from the group consisting of compounds of the formula:

$$\text{(Ia)}$$

in which:
$R_1$ is selected from hydrogen, chlorine, methyl, hydroxyethyl, dimethyl, methoxy, trimethoxy and 3,4 benzo,
$R_2$ is selected from hydrogen and methyl, $R_4$ is selected from hydrogen, trifluoromethyl and methoxy, $R_5$ is selected from $C_{1-3}$ alkyl and phenyl, X is selected from oxygen and sulfur, n is an integer from 1 to 3 inclusive, and a pharmaceutically acceptable acid addition salt thereof, and a therapeutically acceptable excipient.

5. A compound selected from the group consisting of:
a. 1-[N(1-phenoxy-2-propyl) piperazino]-1-phenyl-2-propanol
b. 1-[N(3-phenoxy-1-propyl) piperazino]-1-phenyl-2-propanol
c. 1-[N(3-phenylthio-1-propyl) piperazino]-1-phenyl-2-pentanol
d. 1-[N(2-phenoxy-1-ethyl) piperazino]-1-phenyl-2-phenyl-2-ethanol
e. 1-[N(2-phenoxy-1-ethyl) piperazino]-1-(3-trifluoromethylphenyl)-2-propanol
f. 1-[N-2(4-chloro-phenoxy)-1-ethyl-piperazino]-1-phenyl-2-propanol
g. 1-[N-2(2-methyl-phenoxy-(1-ethyl-piperazino]-1-phenyl-2-propanol
h. 1-[N-2(3-methoxy-phenoxy)-1-ethyl-piperazino]-1-phenyl-2-propanol
i. 1-[N-2(2-naphthyloxy)-1-ethyl-piperazino]-1-phenyl-2-propanol
j. 1-[N-2(4-methyl-phenoxy)-1-ethyl-piperazino]-1-phenyl-2-propanol
k. 1-[N-2(3-β hydroxyethyl-phenoxy)-1-ethyl-piperazino]-1-phenyl-2-propanol
l. 1-[N-2(2-chloro-phenoxy)-1-ethyl-piperazino]-1-phenyl-2-phenyl-2-ethanol
m. 1-[N-2(3,4,5-trimethoxy-phenoxy)-1-ethyl-piperazino]-1-phenyl-2-phenyl-2-ethanol
n. 1-[N(2-phenoxy-1-ethyl) piperazino]-1(4-methoxyphenyl)-2 propanol
o. 1-[N-2(2-methyl-phenoxy)-1-ethyl-piperazino]-1-phenyl-2-phenyl-2-ethanol
p. 1-[N-2(2,6-dimethyl-phenoxy)-1-ethyl-piperazino]-1-phenyl-2-phenyl-2-ethanol
q. 1-[N-2(2,6-dimethyl-phenoxy)-1-ethyl-piperazino]-1-phenyl-2-butanol
r. 1-[N-2(2,6-dimethyl-phenoxy)-1-ethyl-piperazino]-1-phenyl-2-propanol
s. 1-[N(2-phenoxy-1-ethyl) piperazino]-1-phenyl-2-butanol
t. 1-[N(3-phenoxy-1-propyl) piperazino]-1-phenyl-2-phenyl-2-ethanol
u. 1-[N-2(4-chloro-phenylthio)-1-ethyl-piperazino]-1-phenyl-2-butanol
v. 1-[N(2-phenylthio-1-ethyl) piperazino]-1-phenyl-2-propanol
w. 1-[N(2-phenylthio-1-ethyl) piperazino]-1-phenyl-2-phenyl-2-ethanol
x. 1-[Nλλ -2(4-chloro-phenylthio)-1-ethyl-piperazino]-1-phenyl-2-phenyl-2-ethanol
y. 1-[N-2(4-chloro-phenylthio)-1-ethyl-piperazino]-1-phenyl-2-propanol
z. 1-[N(2-phenylthio-1-ethyl) piperazino]-1-phenyl-2-butanol
aa. 1-[N(2-phenoxy-1-ethyl) piperazino]-1-phenyl-2-pentanol
bb. 1-[N-3(2-methyl-phenoxy)-1-propyl-piperazino]-1-phenyl-2-butanol
cc. 1-[N-3(2-methyl-phenoxy)-1-propyl-piperazino]-1-phenyl-2-pentanol and their pharmaceutically acceptable acid addition salts.

* * * * *